United States Patent
Ishimaru (10) Patent No.: US 9,513,165 B2
(45) Date of Patent: Dec. 6, 2016

(54) SPECTROSCOPIC MEASUREMENT DEVICE

(71) Applicant: NATIONAL UNIVERSITY CORPORATION KAGAWA UNIVERSITY, Takamatsu-shi, Kagawa (JP)

(72) Inventor: Ichiro Ishimaru, Takamatsu (JP)

(73) Assignee: NATIONAL UNIVERSITY CORPORATION KAGAWA UNIVERSITY, Takamatsu-shi (JP)

(*) Notice: Subject to any disclaimer, the term of this patent is extended or adjusted under 35 U.S.C. 154(b) by 6 days.

(21) Appl. No.: 14/431,573

(22) PCT Filed: Sep. 25, 2013

(86) PCT No.: PCT/JP2013/075904
§ 371 (c)(1),
(2) Date: Mar. 26, 2015

(87) PCT Pub. No.: WO2014/054488
PCT Pub. Date: Apr. 10, 2014

(65) Prior Publication Data
US 2015/0260573 A1    Sep. 17, 2015

(30) Foreign Application Priority Data

Oct. 1, 2012  (JP) ................ 2012-219760

(51) Int. Cl.
*G01J 3/26*    (2006.01)
*A61B 5/145*   (2006.01)
(Continued)

(52) U.S. Cl.
CPC ............... *G01J 3/26* (2013.01); *A61B 5/1455* (2013.01); *A61B 5/14532* (2013.01);
(Continued)

(58) Field of Classification Search
CPC  G01J 3/0213; A61B 5/14532; A61B 5/7257
See application file for complete search history.

(56) References Cited

U.S. PATENT DOCUMENTS 3,973,849 A    8/1976  Jackson et al.
6,477,393 B1   11/2002 Chou

FOREIGN PATENT DOCUMENTS

JP   H06-281499 A   10/1994
JP   H09-113211 A   5/1997
(Continued)

OTHER PUBLICATIONS

Dec. 3, 2013 International Search Report issued in International Patent Application No. PCT/JP2013/075904.
(Continued)

*Primary Examiner* — Kara E Geisel
*Assistant Examiner* — Shawn Decenzo
(74) *Attorney, Agent, or Firm* — Oliff PLC (57) ABSTRACT

A spectroscopic measurement device includes a dark filter that is arranged on an optical path between an imaging optical system and a light detection unit and includes a plurality of regions having different transmittances, the filter being configured such that a fixed reflected measurement light and a movable reflected measurement light that are guided to a same point by the imaging optical system and form interference light are transmitted through a same region; and an arithmetic processing unit that obtains an interferogram of the measurement light at a transmittance corresponding to each of two or more regions from a detection signal of each pixel of a light detection unit when a movable reflection unit is moved, and obtains a spectrum of the measurement light based on the interferogram.

4 Claims, 8 Drawing Sheets

(51) Int. Cl.

| | | |
|---|---|---|
| *A61B 5/1455* | (2006.01) | |
| *G01J 3/453* | (2006.01) | |
| *G01N 21/359* | (2014.01) | |
| *G01N 21/47* | (2006.01) | |
| *G01N 21/49* | (2006.01) | |
| *G01J 3/02* | (2006.01) | |
| *A61B 5/00* | (2006.01) | |
| *G01J 3/45* | (2006.01) | |
| *G01N 21/35* | (2014.01) | |
| *G01J 3/12* | (2006.01) | |

(52) U.S. Cl.
CPC ........ *A61B 5/14546* (2013.01); *A61B 5/7257* (2013.01); *G01J 3/0205* (2013.01); *G01J 3/0213* (2013.01); *G01J 3/45* (2013.01); *G01J 3/4532* (2013.01); *G01J 3/4535* (2013.01); *G01N 21/359* (2013.01); *G01N 21/4738* (2013.01); *G01N 21/49* (2013.01); *A61B 2562/0238* (2013.01); *F04C 2270/0421* (2013.01); *G01J 2003/1213* (2013.01); *G01N 2021/3595* (2013.01)

(56) References Cited

FOREIGN PATENT DOCUMENTS

| | | |
|---|---|---|
| JP | 2008-309706 A | 12/2008 |
| JP | 2008-309707 A | 12/2008 |
| JP | 2009-133735 A | 6/2009 |
| JP | 2010-271246 A | 12/2010 |
| KR | 10-2009-0056858 A | 6/2009 |

OTHER PUBLICATIONS

Jun. 24, 2014 International Preliminary Report on Patentability issued in PCT/JP2013/075904.

Jul. 21, 2015 Extended Search Report issued in European Patent Application No. 13843910.4.

Kojima, Daisuke et al., "Spectroscopic tomography of biological tissues with the near-infrared radiation for the non-invasive measurement of the biogenic-substances", Optical Diagnostics and Sensing XII: Toward Point-of-Care Diagnostics; and Design and Performance Validation of Phantoms Used in Conjunction with Optical Measurement of Tissue IV, Feb. 9, 2012, 2012 SPIE, Proc. of SPIE, XP 060002140, vol. 8229, No. 1, pp. 1-7.

Fig. 9A FRONT VIEW

Fig. 9B SIDE VIEW

Fig. 9C THREE-DIMENSIONAL SHAPE OF DIFFRACTED LIGHT

SPECTROSCOPIC MEASUREMENT DEVICE

TECHNICAL FIELD

The present invention relates to a spectroscopic measurement device, and, more particularly, to a spectroscopic measurement device that can non-invasively measure biological components such as blood sugar and blood cholesterol.

BACKGROUND ART

In various diseases such as diabetes and hyperlipidemia, a control amounts of biological components such as glucose (blood sugar) and cholesterol included in blood is important to prevent and treat the diseases. However, to measure amounts of biological components in blood, a small amount of blood usually needs to be drawn, which is painful. And troublesome operations, such as sterilization of a blood drawing area and proper treatment of consumables, are necessary, so that, frequent blood drawing for the measurement of amounts of biological components for preventive purposes, for example, is apt to be averted.

Consequently, a non-invasive measurement device that measures amounts of biological components without drawing blood is proposed (see Patent Literature 1). In the measurement device, light is cast to a biological tested area, whereby biological components are detected using spectral characteristics of light (object light) emitted from the biological components inside of the tested area. Specifically, object light, including transmitted light and diffused/scattered light, generated from each bright point that optically forms the biological components is introduced through an objective lens to a phase shifter composed of a fixed mirror unit and a movable mirror unit, and object beams reflected from the two mirror units interfere with each other on an imaging plane. The movable mirror unit is moved by a piezo element or the like, and a phase shift according to the moving distance of the movable mirror unit is given to the object beams reflected from the fixed mirror unit and the movable mirror unit. Accordingly, the intensity of the interference light is changed, and a so-called interferogram is acquired. The interferogram is Fourier-transformed to obtain the spectral characteristics (spectrum) of the object light.

CITATION LIST

Patent Literature

[Patent Literature 1] JP 2008-309707 A

SUMMARY OF INVENTION

Technical Problem

The interference light formed on the imaging plane is received by a light detection unit, and is output as an analog signal. The signal is amplified by an amplifier, and is then converted into digital data by an A/D converter. The digital data is subjected to predetermined data processing, and is then Fourier-transformed, so that a spectrum is obtained. In the case of examining a change in amounts of biological components, it is necessary to obtain a spectrum with small noise by highly accurately detecting transmitted light and the like from the biological components. To achieve this, it is preferable to amplify the analog signal from the light detector as much as possible, but, if the input range of the A/D converter is exceeded, an overflow occurs, leading to saturation. Hence, the largest amount of light emitted from the biological components is assumed, and the amplification factor is set based on the assumed largest amount.

However, in the case of continuously measuring the concentrations of glucose and cholesterol included in blood and examining changes in the concentrations, if the measurement is continued at a constant amplification factor, the amplification factor used for the measurement is not necessarily proper. In particular, in the case where the amount of light emitted from a tested area is small, tiny changes in the concentrations of glucose and cholesterol cannot be accurately measured.

A problem to be solved by the present invention is to provide a spectroscopic measurement device that can measure light emitted from an object to be measured in a wide measurement range.

Solution to Problem

To solve the aforementioned problem, the present invention provides a spectroscopic measurement device including:

a) a fixed reflection unit;

b) a movable reflection unit that has a reflection surface parallel to a reflection surface of the fixed reflection unit and is movable in a direction perpendicular to the reflection surface of the fixed reflection unit;

c) an incident optical system that causes measurement light emitted from each of a plurality of measurement points inside of an object to be measured to enter the reflection surface of the fixed reflection unit and the reflection surface of the movable reflection unit;

d) an imaging optical system that introduces fixed reflected measurement light reflected by the reflection surface of the fixed reflection unit and movable reflected measurement light reflected by the reflection surface of the movable reflection unit to the same point and forms interference light of the two reflected measurement lights;

e) a light detection unit including a plurality of pixels for detecting intensities of the interference lights each of which is generated from the measurement light emitted from each of the plurality of the measurement points;

f) a dark filter that is arranged on an optical path between the imaging optical system and the light detection unit and includes a plurality of regions having different transmittances, the filter being configured such that the fixed reflected measurement light and the movable reflected measurement light that are guided to the same point by the imaging optical system and form the interference light are transmitted through the same region; and g) an arithmetic processing unit that obtains an interferogram of the measurement light at a transmittance corresponding to each of the two or more regions from a detection signal of each pixel of the light detection unit when the movable reflection unit is moved, and obtains a spectrum of the measurement light based on the interferogram.

According to the configuration, fixed reflected measurement light and movable reflected measurement light that form interference light are transmitted through a region having the same light transmittance in the filter, and the interference light is detected. Then, an interferogram is obtained from a detection signal of the interference light, and a spectrum of the measurement light is obtained. Accordingly, through one measurement, interference lights having intensities respectively corresponding to the plurality of regions having different light transmittances are detected, interferograms are acquired, and a spectrum of measurement light can be obtained from an optimum interferogram of the acquired interferograms.

Advantageous Effects of Invention

According to the present invention, it is possible to achieve a dynamic range of a spectroscopic measurement device while preventing an overflow in which the input range of an A/D converter is exceeded.

DESCRIPTION OF EMBODIMENTS

Hereinafter, specific embodiments applying the present invention to a blood sugar level sensor will be described with reference to the drawings.

First Embodiment

Figure 1:
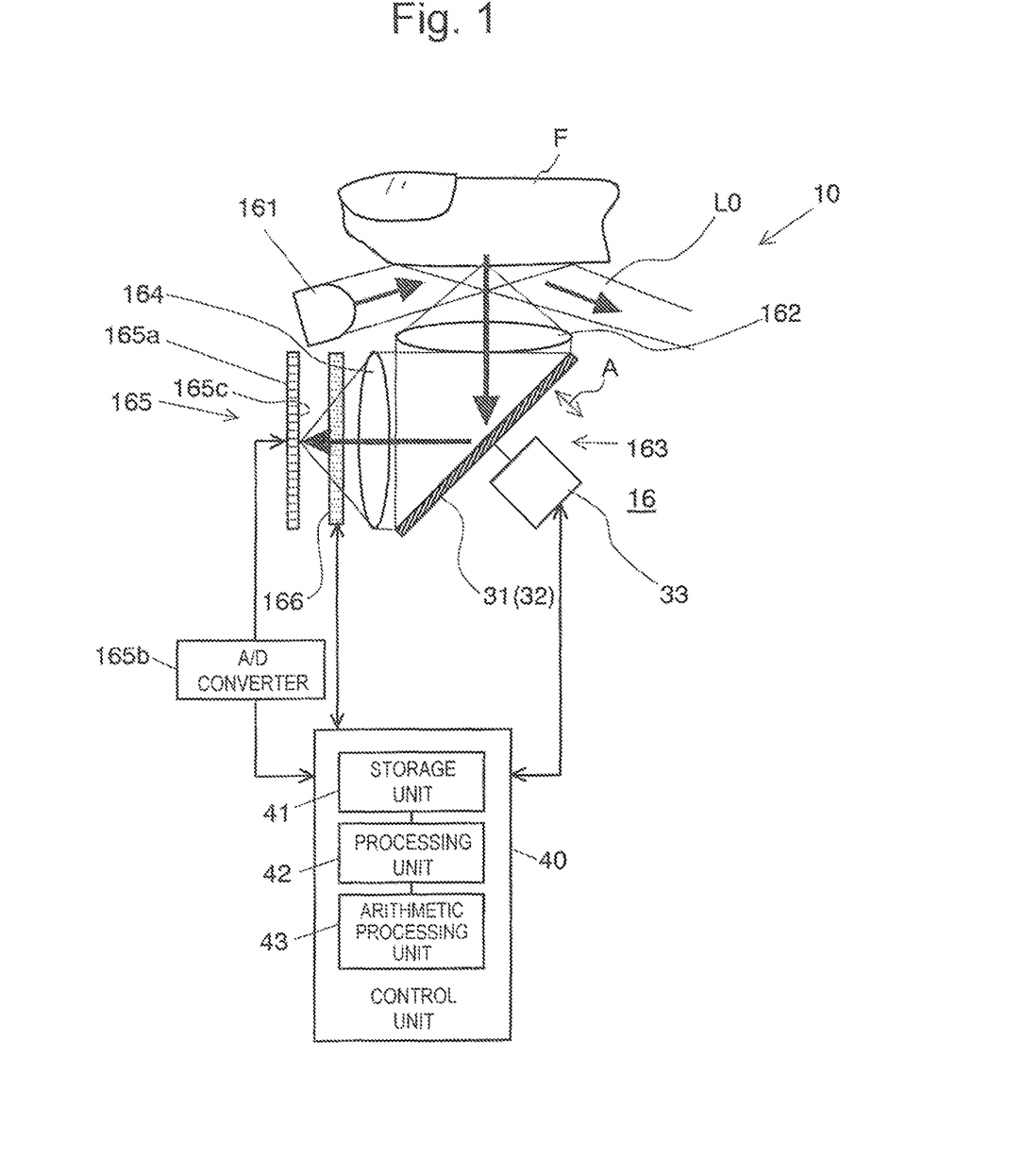
FIG. 1 is a schematic view showing an overall configuration of a blood sugar level sensor according to a first embodiment of the present invention.

FIG. 1 shows an overall configuration of a blood sugar level sensor 10 according to a first embodiment. The blood sugar level sensor 10 includes spectroscopic measurement unit 16 and a control unit 40 that controls an operation of the spectroscopic measurement unit 16.

The spectroscopic measurement unit 16 includes a light source 161, an objective lens 162, a phase shifter 163, an imaging lens 164, a detection unit 165, and a light reducing device 166. In the present embodiment, the objective lens 162 and the imaging lens 164 are equivalent to an incident optical system and an imaging optical system, respectively.

The objective lens 162 is arranged to face the light casting surface of a fingertip F. The imaging lens 164 is arranged such that the optical axis is orthogonal to the objective lens 162.

A light source with good permeability to the skin that emits near-infrared light at a wavelength of around 1 μm is used as the light source 161. When emission light from the light source 161 is cast to the fingertip F that is an object to be measured, the emission light is transmitted through the skin of the fingertip F, and generates reflected light and scattered light resulting from various optical phenomena, inside of the fingertip F. These lights are transmitted again through the skin, are emitted to the outside of the fingertip F, enter the objective lens 162, and are converted into parallel beams.

The detection unit 165 includes, for example: a two-dimensional CCD camera 165a of 16×16 pixels; an amplifier (not shown) that amplifies a received light signal of the CCD camera 165a; and an A/D converter 165b that A/D-converts the amplified received light signal. A light-receiving surface 165c of the CCD camera 165a is arranged so as to coincide with the imaging plane of the imaging lens 164.

A detection signal of the detection unit 165 is stored in a storage unit 41. As will be described in detail later, a processing unit 42 reads out the detection signal stored in the storage unit 41, and obtains an interferogram. An arithmetic processing unit 43 mathematically Fourier-transforms the interferogram, and as a result, spectral characteristics (spectrum) as relative intensity at each wavelength of measurement light are obtained.

The phase shifter 163 is arranged between the objective lens 162 and the imaging lens 164. The phase shifter 163 includes a fixed mirror unit 31, a movable mirror unit 32, and a drive mechanism 33 that moves the movable mirror unit 32. Each of the fixed mirror unit 31 and the movable mirror unit 32 has a rectangular reflection surface inclined at an angle of 45° relative to the optical axis of the objective lens 162 and the optical axis of the imaging lens 164. The reflection surfaces of the mirror units are aligned at a very small gap.

The drive mechanism 33 includes, for example, a piezo element including a capacitance sensor. The drive mechanism 33 receives a signal from the control unit 40 and moves the movable mirror unit 32 in an arrow A direction while maintaining the inclination angle of the reflection surface relative to the optical axis at 45°. According to the configuration, the position of the movable mirror unit 32 relative to the fixed mirror unit 31 is changed, and a phase difference is provided between the light reflected by the fixed mirror unit 31 and the light reflected by the movable mirror unit 32.

Specifically, t the moving distance of the movable mirror unit 32 in the optical axis direction of the objective lens 162 or the imaging lens 164 is $1/\sqrt{2}$ of the moving distance of the movable mirror unit 32 in the arrow A direction. The optical path length difference that provides relative phase change between the light reflected by the fixed mirror unit 31 and the light reflected by the movable mirror unit 32 is twice the moving distance of the movable mirror unit 32 in the optical axis direction.

The light reducing device 166 is arranged between the imaging lens 164 and the detection unit 165. The light reducing device 166 includes: a rectangular plate-like dark filter 166a (see FIG. 3) in which a plurality of regions having transmittances that change in a stepwise manner are arranged in a lateral direction; and a stepping motor that moves the dark filter 166a in a straight direction by means of a rack and a pinion. A control table showing a relationship between the transmittance of the dark filter 166a and the number of steps of the stepping motor is stored in advance in the storage unit 41. Accordingly, when the dark filter 166a is set to a target transmittance, the control unit 40 drives the stepping motor into a number of steps obtained from the control table.

Next, an operation of using the blood sugar level sensor 10 with the previously described configuration to measure the blood sugar (glucose) in the blood of a fingertip of a test subject will be described.

First, the fingertip F of the test subject is placed at a predetermined position, and near-infrared light from the light source 161 is cast to the fingertip F. Consequently, the near-infrared light is transmitted through the skin of the fingertip F, and is scattered by various biological components inside of the fingertip F. The light scattered by the biological components passes again through the skin of the fingertip F, and is emitted to the outside.

The surfaces (reflection surfaces) of the fixed mirror unit 31 and the movable mirror unit 32 of the phase shifter 163 are positioned on the same plane in an initial state immediately after measurement start. For example, a region having an intermediate transmittance (40%) among the plurality of regions of the dark filter 166a is positioned on the optical paths of the imaging lens 164 and the detection unit 165. After that, when a measurement operation is started, as will be describe later, the control unit 40 drives the drive mechanism 33 to move the movable mirror unit 32, and drives the light reducing device 166 to move the dark filter 166a such that a region having a set proper transmittance is positioned on the optical paths of the imaging lens 164 and the detection unit 165.

The scattered light as measurement light emitted from the inside of the fingertip F reaches the objective lens 162 while spreading in various directions, become parallel beams, and reach the entire surfaces of the fixed mirror unit 31 and the movable mirror unit 32 of the phase shifter 163. More specifically, part of the scattered light is reflected by the reflection surface of the fixed mirror unit 31, and the rest of the scattered light is reflected by the reflection surface of the movable mirror unit 32. Both of the scattered lights enter the imaging lens 164, respectively. In the following description, the scattered light reflected by the fixed mirror unit 31 will also be called a fixed scattered light, and the scattered light reflected by the movable mirror unit 32 will also be called a movable scattered light.

Figure 2:
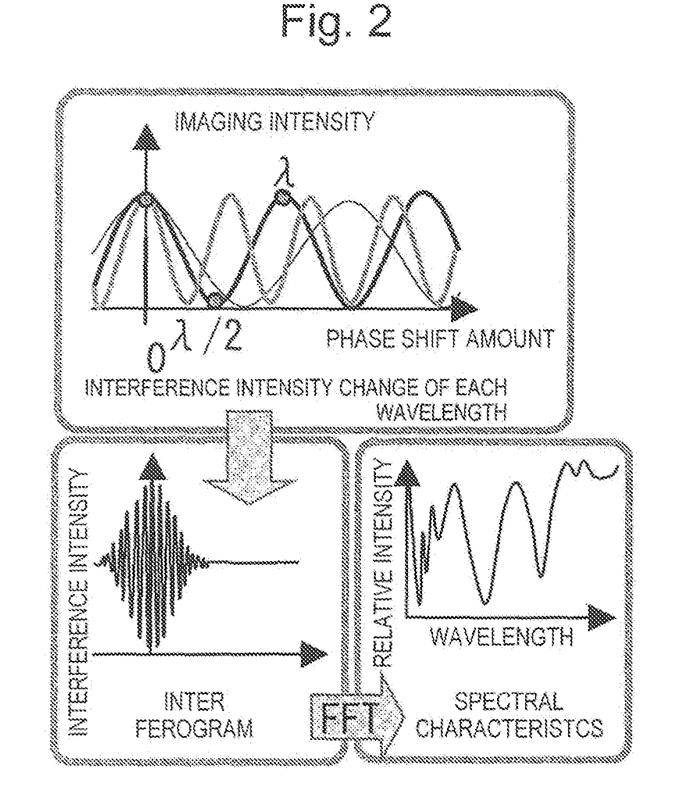
FIG. 2 is a view for describing a relationship among a change in interference light intensity, an interferogram, and spectral characteristics.

The fixed scattered light beam and the movable scattered light beam that enter the imaging lens 164 enter the light-receiving surface 165c of the detection unit 165 through the dark filter 166a, and interfere with each other. In this case, the scattered light emitted from the inside of the fingertip F contains various wavelengths of light. Therefore, the movable mirror unit 32 can be moved to change the optical path length difference between the movable scattered light beam and the fixed scattered light beam to obtain a waveform of a change in the intensity of the image (a change in the intensity of interference light) called an interferogram. The interferogram can be mathematically Fourier-transformed to obtain spectral characteristics. FIG. 2 shows the change in the intensity of the light at each wavelength, the interferogram, and the spectral characteristics.

In the blood sugar level sensor 10 of the present embodiment, only the scattered light emitted from the focal plane of the objective lens 162 positioned at a specific depth inside of the fingertip F is focused on the light-receiving surface 165c of the detection unit 165, and the light generated from other part than the focal planes is not focused on the light-receiving surface 165c of the detection unit 165. Therefore, spectral characteristics inside of the fingertip, in which the depth is limited only to the focal plane, can be obtained.

The lights that enter the light-receiving surface 165c of the detection unit 165 and interfere with each other are output as an analog signal. The signal is converted into digital data by the A/D converter 165b, and is input to the arithmetic processing unit 43 of the control unit 40. The arithmetic processing unit 43 performs predetermined data processing on the digital data, and then Fourier-transforms the digital data, so that spectral characteristics (spectrum) are obtained.

Meanwhile, the intensity of the interference light formed on the light-receiving surface 165c of the detection unit 165 changes (increases/decreases) in accordance with the blood sugar level. An analog signal of low-intensity interference light has a low signal intensity. Hence, if the analog signal is input to the arithmetic processing unit 43 without any change, the signal intensity cannot be measured with good sensitivity. For this reason, the analog signal of the interference light is amplified by the amplifier (not shown), and is then input to the A/D converter 165b. However, in the case of a high interference light intensity, the amplified analog signal may exceed the input range of the A/D converter 165b, and an overflow may occur, leading to saturation.

To prevent this, the control unit 40 drives the stepping motor to move the dark filter 166a such that the dark filter 166a is set to a proper transmittance. From the set transmittance of the dark filter 166a, the arithmetic processing unit 43 obtains an interferogram when the transmittance is 100%. Accordingly, in the present embodiment, the arithmetic processing unit 43 functions as compensation means. Then, the arithmetic processing unit 43 Fourier-transforms the corrected interferogram to obtain spectral characteristics.

Specifically, based on the interference light intensity of measurement light that is detected by the detection unit 165 in an initial state, the arithmetic processing unit 43 sets the proper transmittance of the light reducing device 166 such that the interference light intensity becomes a maximum value within the input range of the detection unit 165 (A/D converter). Accordingly, in the present embodiment, the arithmetic processing unit 42 functions as setting means. The set proper transmittance is stored in the storage unit 41. The control unit 40 reads the proper transmittance stored in the storage unit 41, and drives the stepping motor to move the dark filter 166a. Accordingly, in the subsequent measurement operation, interference light of measurement light that passes through a region having the proper transmittance of the dark filter 166a enters the detection unit 165. In this way, the input range of the detection unit 165 can be effectively utilized, and an overflow in which the input range is exceeded can be prevented.

Figure 4:
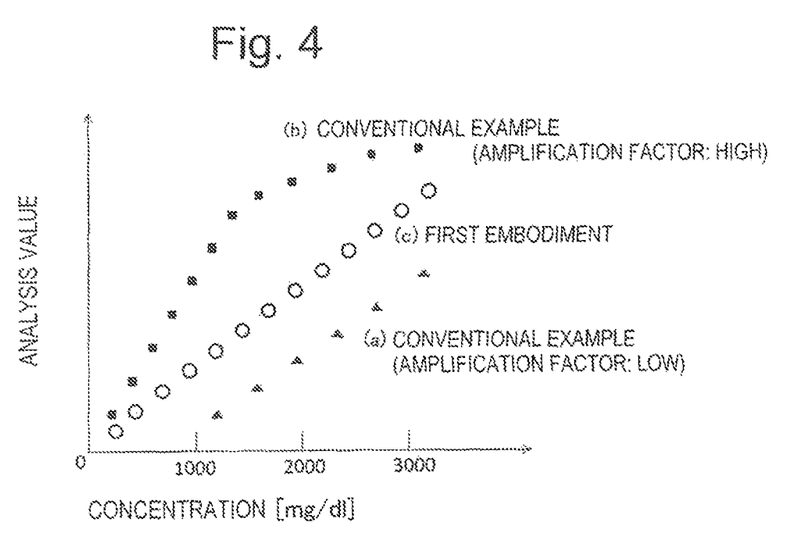
FIG. 4 is a comparison view between an analysis result of the blood sugar level sensor according to the first embodiment and analysis results of a conventional blood sugar level sensor.

FIG. 4 shows a result obtained by measuring and analyzing the glucose concentration in a test tube using the blood sugar level sensor 10 of the present embodiment. In a conventional example (in which the light reduction rate of a dark filter is constant or a dark filter is not provided), if the amplification factor is made lower so as to suit an analog signal of high-intensity interference light, a low-concentration region falls below the detection limit ((a) in FIG. 4). If the amplification factor is made higher so as to suit an analog signal of low-intensity interference light, saturation occurs in a high-concentration region ((b) in FIG. 4). On the other hand, in the present embodiment in which the transmittance of the dark filter 166a is variable, proper measurement is possible in every concentration region ((c) in FIG. 4).

Second Embodiment

A main configuration of a blood sugar level sensor of a second embodiment is similar to that of the first embodiment shown in FIG. 1, and hence illustration and detailed description thereof are omitted. In the present embodiment, reflected measurement light is transmitted through the entire surface of the dark filter 166a including the plurality of regions having different transmittances, whereby an interferogram is obtained. Accordingly, unlike the first embodiment, the dark filter 166a is not moved in the present embodiment. Moreover, similarly to the first embodiment, the two-dimensional CCD camera 165a of 16×16 pixels is used, and alternatively, another camera or the like having the number of pixels equal to or more than the number of regions of the dark filter 166a may be used.

Figure 3:
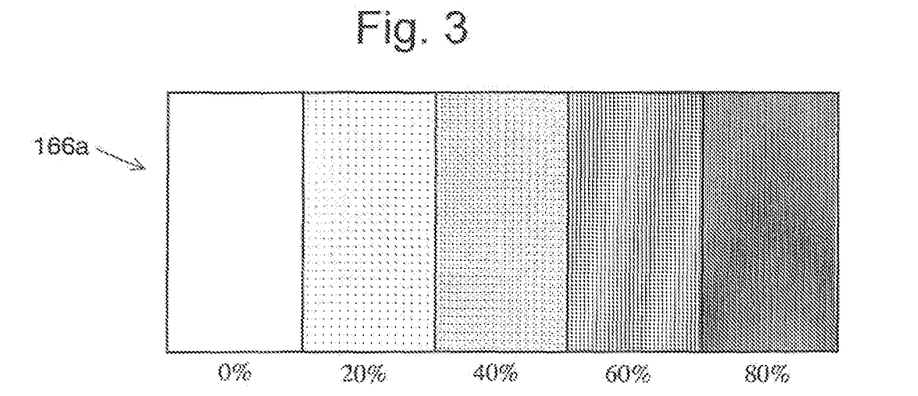
FIG. 3 is a view showing a dark filter.

In the present embodiment, a fixed scattered light beam and a movable scattered light beam that form one interference light (interference image) pass through the same region of the dark filter 166a. In the present embodiment, because the dark filter 166a including five regions having different transmittances is used as shown in FIG. 3, five interference lights having different intensities can be detected by the detection means 165 at the same time, and an interferogram can be obtained for each detected light. Then, a proper transmittance is obtained from the obtained interferograms, and a spectrum is obtained using the interferogram of measurement light that is transmitted through a region having the proper transmittance.

As described above, according to the configuration of the present embodiment, a plurality of interference lights having different intensities are detected through one measurement, and hence more efficient measurement than that in the configuration of the first embodiment is possible.

Third Embodiment

Figure 5A:
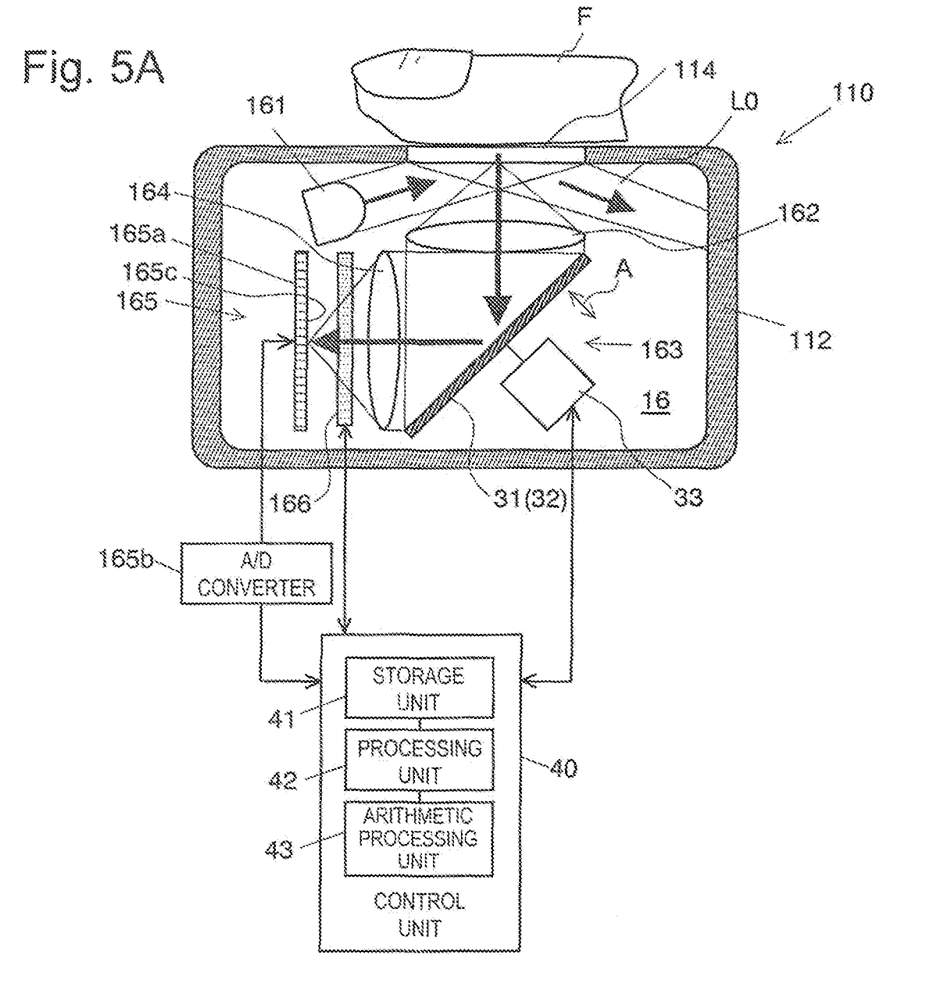
FIG. 5A and FIG. 5B are schematic views showing an overall configuration of a blood sugar level sensor according to a third embodiment of the present invention.
Figure 5B:
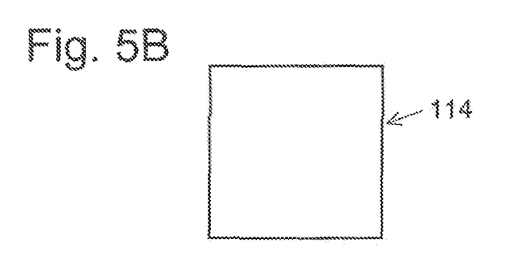

FIG. 5A and FIG. 5B show an overall configuration of a blood sugar level sensor 110 according to a third embodiment. In the blood sugar level sensor 110, the spectroscopic measurement unit 16 is housed in a rectangular box-like casing 112. A rectangular plate-like window 114 is fixed to one (for example, the upper surface) of the peripheral side surfaces of the casing 112.

The casing 112 is made of a material that does not transmit light, such as plastic and metal. The window 114 is made of a light transmissive material such as glass and plastic, and the fingertip F is placed on the upper surface. The light source 161 is arranged in a direction such that specular reflected light LO generated when the emission light is cast to the light casing surface of the window 114 does not enter the objective lens 162.

In the present embodiment, the fingertip F is firmly pressed against the upper surface of the window 114, and measurement is performed with the fingertip F and the window 114 being in a close contact with each other. Hence, the light from the light source 161 enters the inside of the fingertip F through the window 114, and is scattered by various biological components inside of the fingertip F. Then, the scattered light is emitted from the fingertip F, passes again through the window 114 to reach the inside of the casing 112, and enters the objective lens 162 as measurement light. At this time, because the fingertip F is in close contact with the window 114, irregularities on the surface of the fingertip F are planarized, and the light from the light source 161 can be suppressed from being scattered and reflected by the irregularities to mix in the measurement light. Moreover, because the fingertip F is firmly pressed against the window 114, the focal position of the objective lens 162 can be maintained at a predetermined position (depth) in the fingertip F during the measurement. In this way, the blood sugar level sensor 110 according to the present embodiment can accurately measure the blood sugar level.

Fourth Embodiment

FIG. 6A to FIG. 11 show a blood sugar level sensor 210 according to a fourth embodiment of the present invention. Differences from the blood sugar level sensor 110 according to the third embodiment are mainly described below. First, in the blood sugar level sensor 210, a configuration of a window 214 fixed to the upper surface of the casing 112 is different from that of the window 114 in the third embodiment.

Figure 6A:
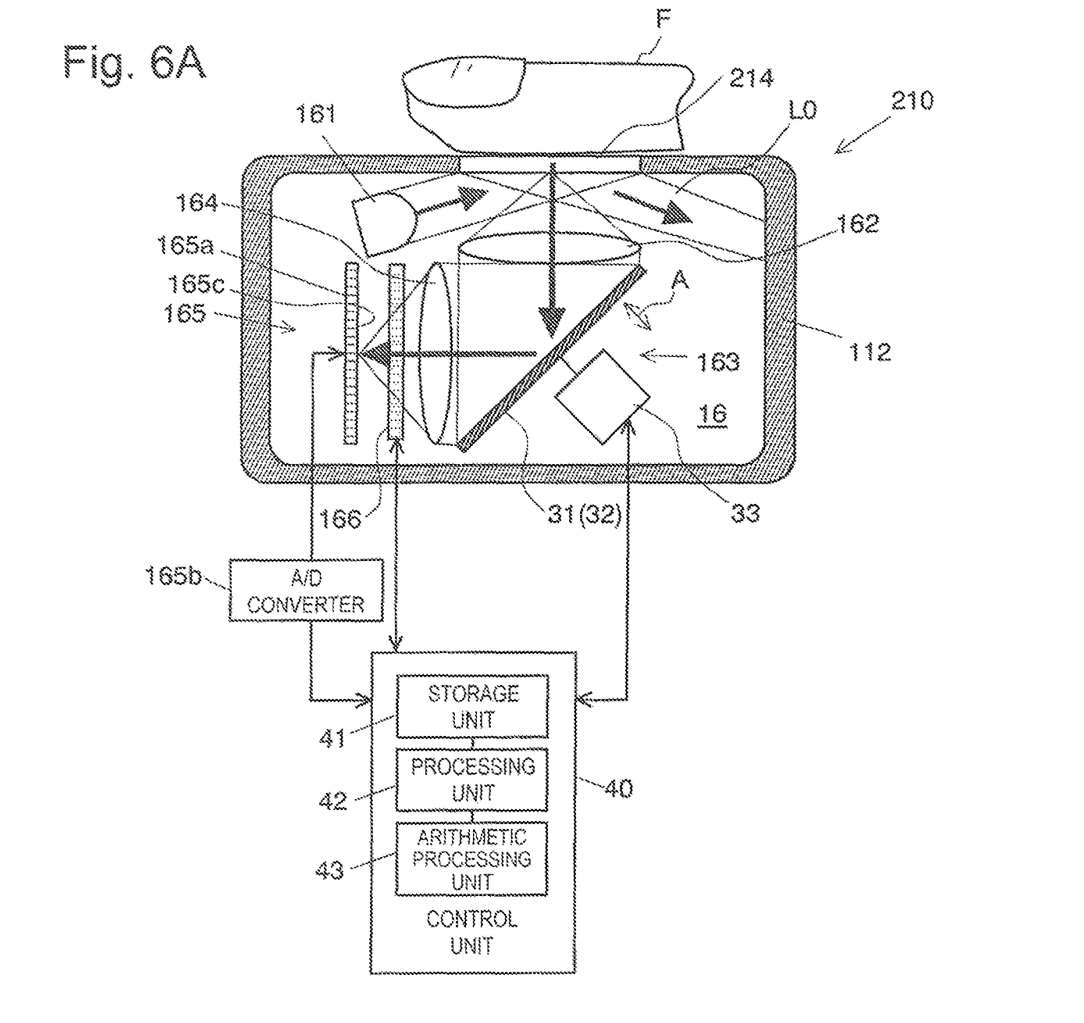
FIG. 6A and FIG. 6B are schematic views showing an overall configuration of a blood sugar level sensor according to a fourth embodiment of the present invention.
Figure 6B:
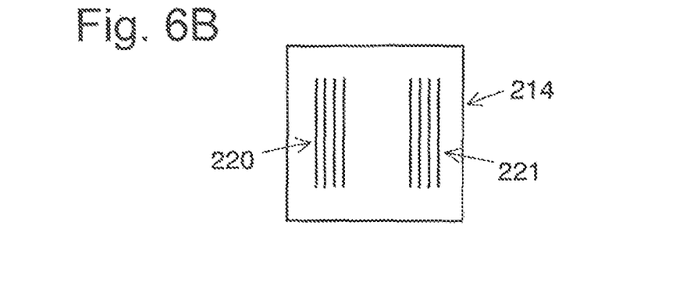

Specifically, as shown in FIG. 6B, diffraction gratings are formed on part of the lower surface (light casting surface) of the window 214 positioned in the casing 112. In this embodiment, two diffraction gratings 220 and 221 extending along two opposing sides of the window 214 are formed. In the following description, areas provided with the two diffraction gratings 220 and 221 in the light casting surface of the window 214 will also be called reference light areas, and the other areas in the light casting surface of the window 214 will also be called measurement light areas. The diffraction gratings 220 and 221 are constructed by a plurality of projection lines parallel to the two sides of the window 214. In the present embodiment, the interval between the projection lines is set to 1.1 μm.

The light source 161 is arranged in a direction such that specular reflected light generated when the emission light is cast to the light casting surface of the window 214 does not enter the objective lens 162 and such that first-order diffracted light generated when the light is cast to the diffraction gratings 220 and 221 enters the objective lens 162. The first-order diffracted light from the diffraction gratings 220 and 221 is used as reference light. The reference light will be described later.

The detection unit 165 includes, for example: the two-dimensional CCD camera 165a of 16×16 pixels; the amplifier (not shown) that amplifies a received light signal of the CCD camera 165a; and the A/D converter 165b that A/D-converts the amplified received light signal. The light-receiving surface 165c of the CCD camera 165a is arranged so as to coincide with the imaging plane of the imaging lens 164.

Figure 7:
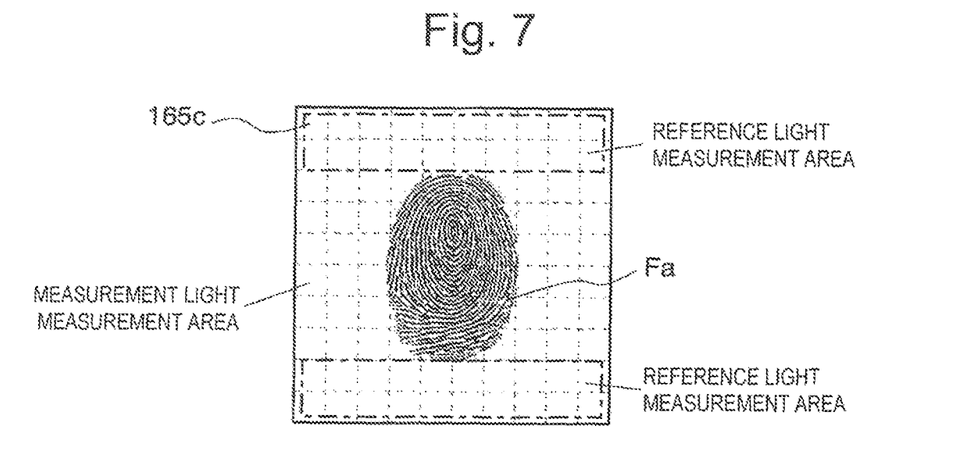
FIG. 7 is a view showing a light-receiving surface of a detection unit.

FIG. 7 is a view schematically showing the light-receiving surface 165c of the detection unit 165. For the convenience, the number of pixels is 10×10 in the description here. As shown in FIG. 7, many CCDs are arranged on the light-receiving surface 165c of the detection unit 165, and the first-order diffracted light (reference light) generated by the diffraction grating 220 and the diffraction grating 221 is focused on top 20 (2×10) CCDs and bottom 20 CCDs, respectively. Accordingly, these CCDs serve as a reference light detection unit. The measurement light is focused on the CCDs of the light-receiving surface 165c excluding the reference light detection unit. Accordingly, these CCDs serve as a measurement light detection unit. Actually, the measurement light is focused on the CCDs positioned at the part indicated by an image Fa of the fingertip F placed on the placement surface of the window 214.

An operation of using the blood sugar level sensor 210 with the previously described configuration to measure the blood sugar (glucose) in the blood of a fingertip of a test subject will be described. Also in the present embodiment, the surfaces (reflection surfaces) of the fixed mirror unit 31 and the movable mirror unit 32 of the phase shifter 163 are positioned on the same plane in an initial state immediately after measurement start, and, for example, a region having an intermediate transmittance (40%) among the plurality of regions of the dark filter 166a is positioned on the optical paths of the imaging lens 164 and the detection unit 165.

First, the fingertip F of the test subject is firmly pressed against the placement surface of the window 214. In this state, near-infrared light from the light source 161 is cast to the window 214. Consequently, the near-infrared light cast to the measurement light area of the window 214 reaches the fingertip through the window 214, is transmitted through the skin of the fingertip, and is scattered by various biological components inside of the fingertip. The light scattered by the biological components passes again through the skin of the fingertip, reaches the inside of the casing 112 from the window 214, and enters the objective lens 162.

The scattered light as measurement light emitted from the inside of the fingertip reaches the objective lens 162 while spreading in various directions, becomes parallel beams, and reaches the entire surfaces of the fixed mirror unit 31 and the movable mirror unit 32 of the phase shifter 163. Then, part of the scattered light is reflected by the reflection surface of the fixed mirror unit 31, and the rest of the scattered light is reflected by the reflection surface of the movable mirror unit 32. Both of the scattered lights enter the imaging lens 164.

The lights (the fixed scattered light beam and the movable scattered light beam) that are respectively reflected by the reflection surfaces of the fixed mirror unit 31 and the movable mirror unit 32 and enter the imaging lens 164 enter the light-receiving surface 165c of the detection unit 165 through the dark filter 166a, and interfere with each other. At this time, the scattered light emitted from the inside of the tested area contains various wavelengths of light. Hence, the movable mirror unit 32 is moved to change the optical path length difference between the movable scattered light beam and the fixed scattered light beam, whereby a waveform of a change in imaging intensity (a change in interference light intensity) called an interferogram can be obtained. The interferogram is mathematically Fourier-transformed, whereby spectral characteristics can be obtained.

Figure 8:
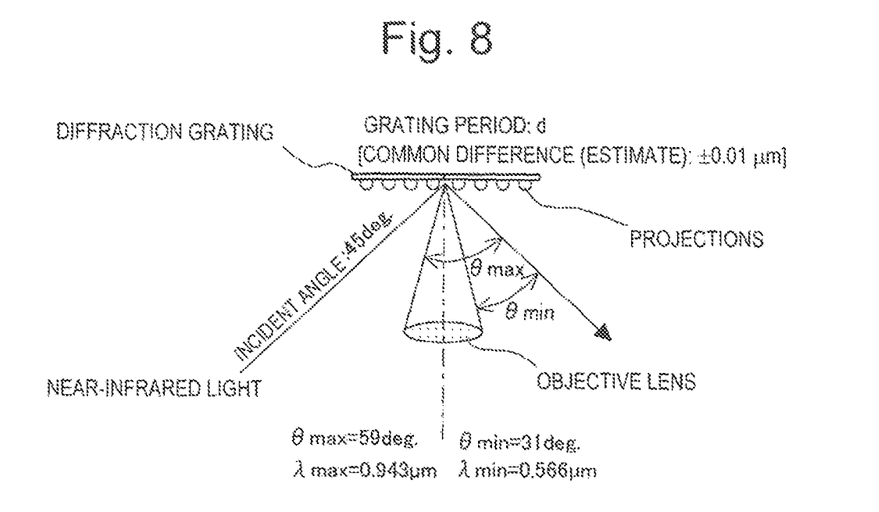
FIG. 8 is an explanatory view of a wavelength and a diffraction angle of first-order diffracted light entering an objective lens from a diffraction grating.

Meanwhile, the near-infrared light cast to the reference light area of the window 214 is reflected by the diffraction gratings 220 and 221, and the first-order diffracted light at a specific wavelength λ enters the objective lens 162. In the present embodiment, as shown in FIG. 8, the near-infrared light from the light source 161 is entered at an incident angle 45 degree relative to the diffraction grating with the spacing of the grating (interval between the projection lines) d=1.1 μm. The objective lens 162 with a numerical aperture N.A.=0.24 (angular aperture=14 degree), a focal distance=20 mm, and a lens aperture g=φ10 mm is used. In this case, a minimum diffraction angle θmin on the short wavelength side entering the objective lens 162 is 31 degree, and a wavelength λmin is 0.566 μm. A maximum diffraction angle θmax on the long wavelength side is 59 degree, and a wavelength λmax is 0.943 μm. In the present embodiment, an InGaAs camera with a detected wavelength region of 0.9 μm to 1.7 μm is used as the detection unit 165. Therefore, of the first-order diffracted light entering the objective lens 162, the wavelength region detected by the detection unit 165 is a very narrow wavelength region (0.9 μm to 0.943 μm).

Figure 9A:
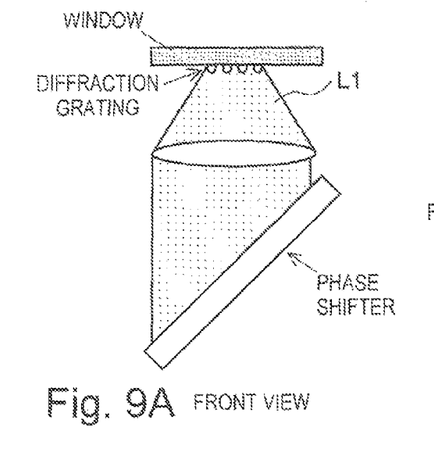
FIG. 9A and FIG. 9B are a front view and a side view showing the first-order diffracted light from the diffraction grating.
Figure 9B:
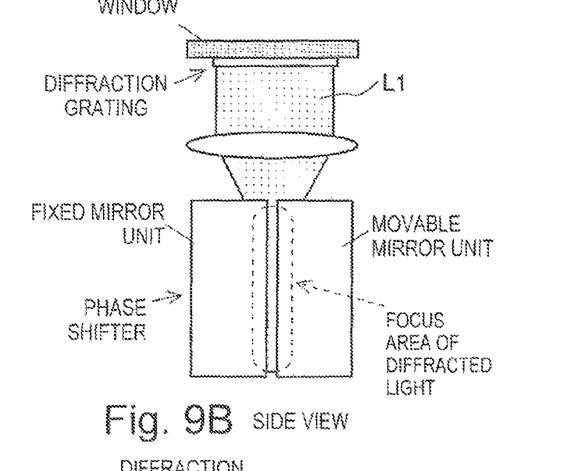
Figure 9C:
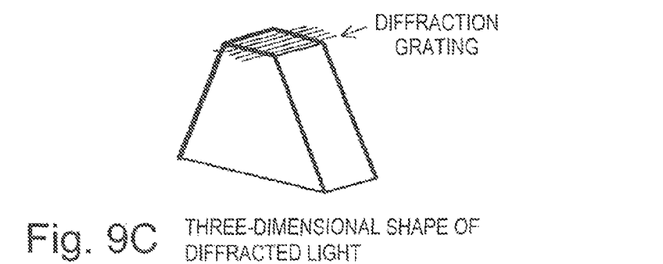
FIG. 9C is a view three-dimensionally showing the first-order diffracted light.

As shown in FIG. 9A, FIG. 9B, and FIG. 9C, the first-order diffracted light from the diffraction gratings 220 and 221 spreads in the width direction of the diffraction gratings 220 and 221 and reaches the objective lens 162 (see the front view of FIG. 9A). Parallel beams reach the objective lens 162 in the extending direction of the diffraction gratings 20 and 21 (see the side view of FIG. 9B). Therefore, the first-order diffracted light in a square pyramid shape as shown in FIG. 9C reaches the objective lens 162. As a result, the first-order diffracted light entering the objective lens 162 forms band-shaped light with a width equivalent to the width of light emitted from the light source 161 and reaches near the boundary of the fixed mirror unit 31 and the movable mirror unit 32. Part of the light is reflected by the reflection surface of the fixed mirror unit 31, and the rest of the light is reflected by the reflection surface of the movable mirror unit 32. Both of the lights enter the imaging lens 164. In the following description, the first-order diffracted light reflected by the fixed mirror unit 31 will also be called fixed diffracted light, and the first-order diffracted light reflected by the movable mirror unit 32 will also be called movable diffracted light.

The fixed diffracted light and the movable diffracted light entering the imaging lens 164 enter the light-receiving surface 165c of the detection unit 165 through the dark filter 166a, and an interference image is formed. At this time, the movable mirror unit 32 can be moved to change the optical path length difference between the fixed diffracted light and the movable diffracted light to obtain a change in the intensity of the interference light. As described, the wavelength regions of the fixed diffracted light and the movable diffracted light are very narrow, and it can be stated that the lights are substantially single-wavelength lights. Therefore, the shape of the change in the intensity of the interference light obtained here is a simple cosine wave.

The light cast to the fingertip F through the window 214 and the light for generating the first-order diffracted light in the diffraction gratings 220 and 221 are emitted from the same light source. Therefore, when there is a fluctuation in the light intensity emitted from the light source 161, both of the change in the intensity of the interference light of the measurement light (scattered light) and the change in the intensity of the interference light of the first-order diffracted light are affected by the fluctuation. The optical path of the measurement light and the optical path of the first-order diffracted light from the window 214 to the detection unit 165 are common. Therefore, when there is a disturbance on the common optical path, both of the change in the intensity of the interference light of measurement light and the change in the intensity of the interference light of the first-order diffracted light are affected by the disturbance.

Consequently, the arithmetic processing unit 43 of the present embodiment corrects the interferogram of measurement light based on: the amplitude of the change in interference light intensity of the first-order diffracted light; and the phase difference between the first-order diffracted light and measurement light at the same wavelength as that of the first-order diffracted light. At this time, the arithmetic processing unit 43 obtains an interferogram when the transmittance is 100%, from the transmittance of the dark filter 166a, and corrects the interferogram. Accordingly, in the present embodiment, the arithmetic processing unit 43 functions as compensation means. Then, the arithmetic processing unit 43 Fourier-transforms the corrected interferogram to obtain spectral characteristics.

Figure 10:
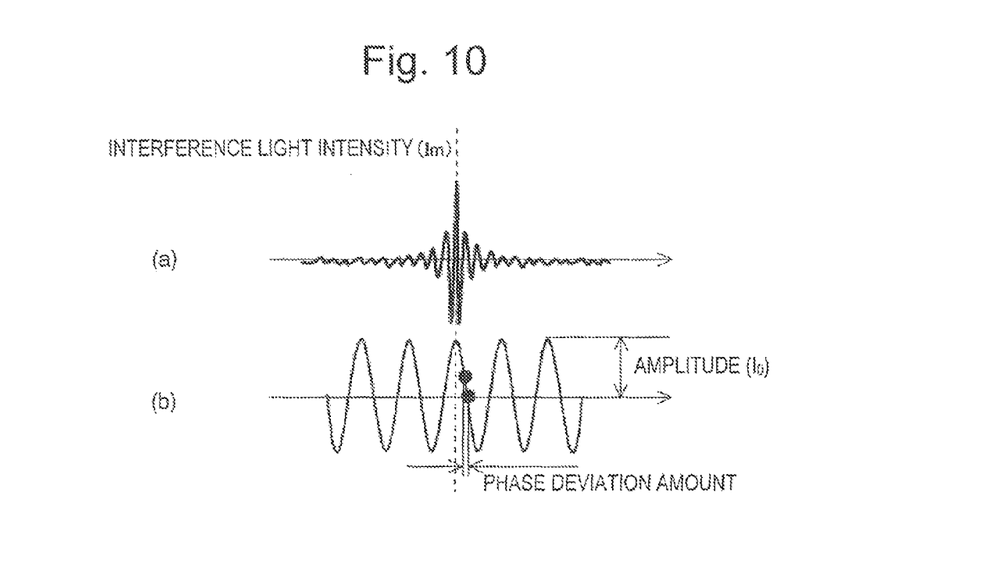
FIG. 10 is a view showing a relationship between (a) the interferogram of measurement light and (b) a change in the intensity of interference light of the first-order diffracted light.
Figure 11:
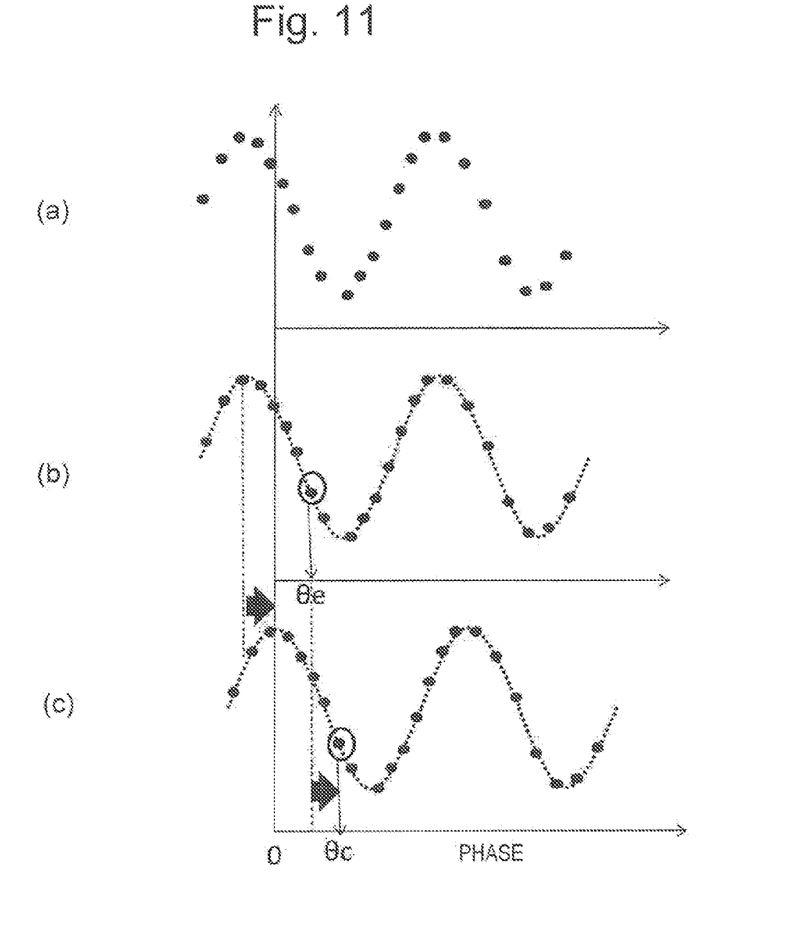
FIG. 11 is explanatory views of a method of correcting the interferogram, (a) shows acquired data, (b) is a view obtained by approximating by a cosine curve, and (c) is a view obtained by shifting the cosine curve.

For example, assuming that an interferogram of measurement light as shown in graph (a) in FIG. 10 and a change in interference light intensity of diffracted light as shown in graph (b) in FIG. 10 are obtained, the interferogram of the measurement light is corrected by using a ratio (Im/Io) of an interference light intensity (Im) of the interferogram of the measurement light to an amplitude (Io) of the change in interference light intensity of the first-order diffracted light. Here, influences of time fluctuations of the light source are the same between Im and Io. Hence, the influences of the time fluctuations of the light source can be suppressed by such correction using Im/Io, so that the measurement accuracy is improved. Moreover, the phase of the interferogram of the measurement light is shifted by the deviation amount of the phase between the first-order diffracted light and the measurement light to correct the interferogram. Specifically, for example, data (graph (a) in FIG. 11) acquired (sampled) for the change in interference light intensity of the first-order diffracted light is first approximated by a cosine curve (wave) (graph (b) in FIG. 11). A phase value of the data at this time is defined as a phase experimental value θe. Subsequently, the cosine curve is shifted (corrected) so as to reach a peak (maximum value) when phase θ=0 (graph (c) in FIG. 11). A phase value of the data at this time is defined as a phase corrected value θc. This correction can suppress influences of a disturbance generated on the optical path, such as an error during a phase shifter operation, so that the measurement accuracy is improved. In this way, the influences of the fluctuations in the light intensity of the light source 161 and the disturbance generated on the optical path can be suppressed, and the interferogram of the measurement light can be accurately obtained.

Further, in the present embodiment, the interference light of the first-order diffracted light is acquired by imaging on the diffraction gratings that are two-dimensionally distributed on part of the plane of the window 214, and hence the measurement accuracy can be improved by a spatial cumulative and averaging effect.

The present invention is not limited to the above-mentioned embodiments, and, for example, the following modifications are possible.

The proper transmittance of the dark filter 166a is obtained from the interference light intensities of measurement light and reference light in an initial state of measurement. Alternatively, a worker may set the transmittance of the dark filter 166a.

In the above-mentioned embodiments, the apparatus that measures blood sugar included in blood of a fingertip is described as an example. Alternatively, the present invention may also be applied to an apparatus that measures the concentration of components in a sample housed in a cell.

Figure 12:
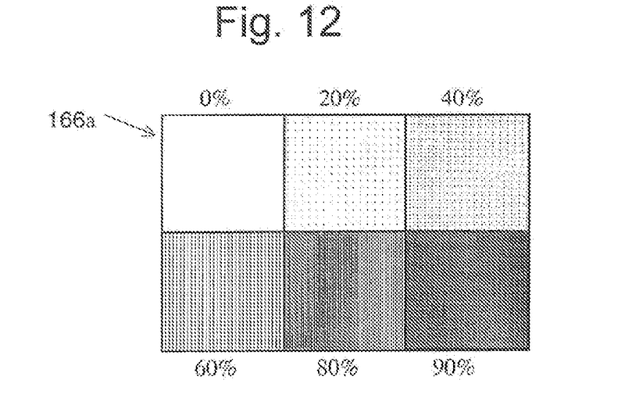
FIG. 12 is a view showing another example of the dark filter.

In the above-mentioned embodiments, the dark filter having a transmittance that changes in a stepwise manner in a lateral direction is used. Alternatively, a dark filter including a plurality of regions having transmittances that are different in a lateral direction and a longitudinal direction may be used as shown in FIG. 12. Still alternatively, a discoid optical filter having a transmittance that changes in a circumferential direction may be used. In this case, the light reducing device can include a stepping motor that moves the optical filter in the circumferential direction. Still alternatively, a dark filter having a continuously changing transmittance may be used.

In the above-mentioned embodiments, a finger is an object to be measured. Alternatively, other biological bodies, for example, other areas of a human body, such as an earlobe, and internal organs can also be an object to be measured. The present invention can be applied to not only medical fields such as blood sugar level measurement of biological bodies but also food fields such as sugar content measurement of fruits and industrial fields such as component measurement of substances.

The dark filter may be arranged between the phase shifter (the movable reflection unit and the fixed reflection unit) and the imaging lens.

REFERENCE SINGS LIST 10, 110, 210 . . . Blood Sugar Level Sensors
112 . . . Casing
114, 214 . . . Window
16 . . . Spectroscopic Measurement Unit
161 . . . Light Source
162 . . . Objective Lens
163 . . . Phase Shifter
164 . . . Imaging Lens
165 . . . Detection Unit
165a . . . CCD Camera
165b . . . A/D Converter
165c . . . Light-Receiving Surface
166 . . . Light Reducing Device
166a . . . Dark Filter
220, 221 . . . Diffraction Gratings
31 . . . Fixed Mirror Unit
32 . . . Movable Mirror Unit
33 . . . Drive Mechanism
40 . . . Control Unit
41 . . . Storage Unit
42 . . . Processing Unit
43 . . . Arithmetic Processing Unit (Compensation Means)
F . . . Fingertrip (Object to be Measured)

The invention claimed is:

1. A spectroscopic measurement device comprising:
a) a fixed reflector;
b) a movable reflector that has a reflection surface parallel to a reflection surface of the fixed reflector and is movable in a direction perpendicular to the reflection surface of the fixed reflector;
c) an incident optical system that causes measurement light emitted from each of a plurality of measurement points inside of an object to be measured to enter the reflection surface of the fixed reflector and the reflection surface of the movable reflector;
d) an imaging optical system that introduces fixed reflected measurement light reflected by the reflection surface of the fixed reflector and movable reflected measurement light reflected by the reflection surface of the movable reflector to the same point and forms interference light of the two reflected measurement lights;
e) a light detector including a plurality of pixels for detecting an intensity of the interference lights, each of which is generated from the measurement light emitted from each of the plurality of the measurement points;
f) a dark filter that is arranged on an optical path between the imaging optical system and the light detector and includes a plurality of regions having different transmittances, the filter being configured such that a plurality of the measurement lights emitted from the plurality of measurement saints are transmitted through n regions (n is equal to or more than two) of the plurality of regions simultaneously, and the fixed reflected measurement light and the movable reflected measurement light that are generated from the same measurement point, are guided to the same point by the imaging optical system, and form the interference light are transmitted through the same region; and
g) a controller including an arithmetic processing unit that obtains an interferogram of the measurement light at a transmittance corresponding to each of the two or more regions from a detection signal of each pixel of the light detector when the movable reflector is moved, and obtains a spectrum of the measurement light based on the interferogram.

2. The spectroscopic measurement device according to claim 1, wherein the arithmetic processing unit is configured to compensate an intensity of the interferogram obtained from the detection signal of each pixel of the light detector, based on a transmittance of the region of the dark filter through which the fixed reflected measurement light and the movable reflected measurement light that are guided to the same point by the imaging optical system and form the interference light are transmitted.

3. The spectroscopic measurement device according to claim 1, wherein the fixed reflected measurement light and the movable reflected measurement light of the measurement light emitted from each of the plurality of measurement points are transmitted through the same region.

4. The spectroscopic measurement device according to claim 2, wherein the fixed reflected measurement light and the movable reflected measurement light of the measurement light emitted from each of the plurality of measurement points are transmitted through the same region.

* * * * *